Figure 1:
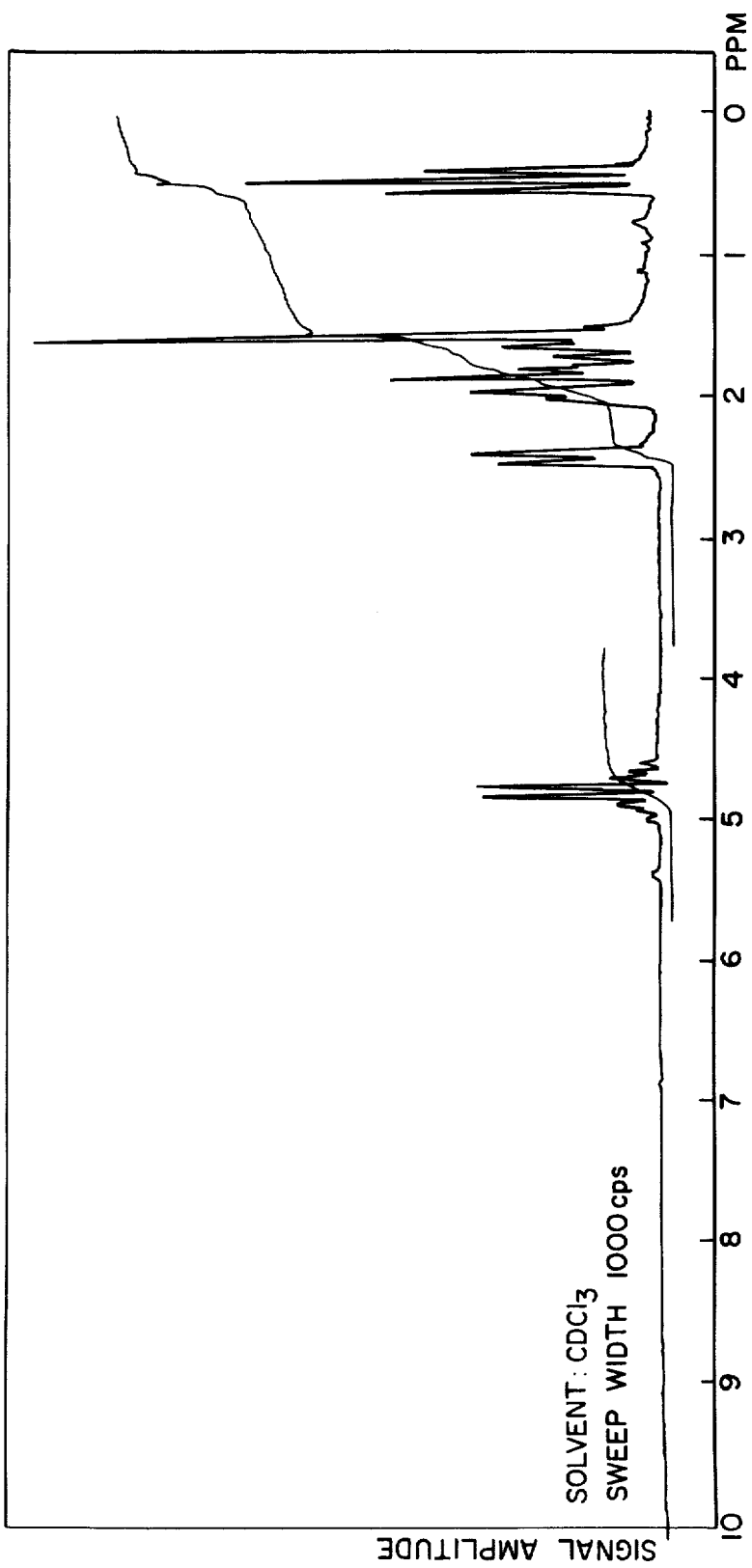

United States Patent [19]

Wiegers et al.

[11] 4,045,489

[45] Aug. 30, 1977

[54] PROCESS FOR PRODUCING CIS-JASMONE

[75] Inventors: Wilhelmus Johannen Wiegers, Red Bank; John B. Hall, Rumson, both of N.J.

[73] Assignee: International Flavors & Fragrances Inc., New York, N.Y.

[21] Appl. No.: 649,544

[22] Filed: Jan. 15, 1976

[51] Int. Cl.$^2$ ............................................. C07C 45/00
[52] U.S. Cl. ............................... 260/586 C; 252/522
[58] Field of Search .................................. 260/586 C

[56] References Cited

U.S. PATENT DOCUMENTS

| 3,668,255 | 6/1972 | Meuly | 260/586 |
| 3,983,175 | 9/1976 | Tamai et al. | 260/586 |

FOREIGN PATENT DOCUMENTS

| 1,059,839 | 2/1967 | United Kingdom | 260/586 C |

OTHER PUBLICATIONS

Tsukasa et al, "Chemical Abstracts", 135501g (1974), cited by applicants.
"Eastman Org. Chemical Bulletin", vol. 48, No. 1, pp. 1-3 (1976).
Jonczyk et al., "Tetrahedron Lett", p. 1351 (1971).
Brandstrom et al., "Tetrahedron Lett", p. 473, (1972).

*Primary Examiner*—Norman Morgenstern
*Attorney, Agent, or Firm*—Arthur L. Liberman; Franklin D. Wolffe

[57] ABSTRACT

A process is described for the preparation of cis-jasmone according to the reaction:

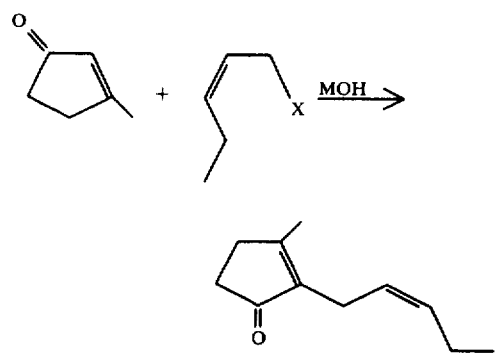

wherein X is chloro or bromo and wherein M is alkali metal, the reaction being carried out (1) using a "phase transfer agent" and (2) in a two phase system.

4 Claims, 2 Drawing Figures

EXAMPLE II

IR SPECTRUM FOR FRACTION 5

PROCESS FOR PRODUCING CIS-JASMONE

BACKGROUND OF THE INVENTION

Cis-jasmone is a valuable substance useful in the formulation of perfume materials.

German Patent 1,244,784, issued on July 20, 1967, discloses the reaction:

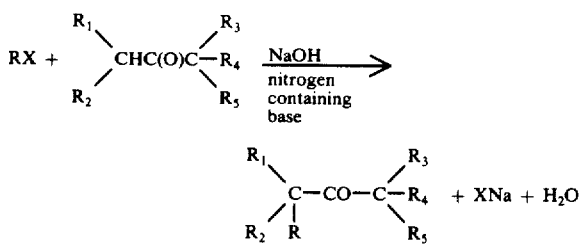

wherein R can be one of alkyl, alkenyl, allyl, propargyl, cyclohexyl or benzyl; X is chloro or bromo and $R_1$, $R_2$, $R_3$, $R_4$, and $R_5$ can be hydrogen, alkyl, alkenyl or phenyl. The reaction of the German Patent is limited to ketones. Although such ketones could be unsaturated, the nature of the reaction is different in kind from the reaction of the instant invention.

Chemical Abstracts, 135501 g, 1974, summarizes a paper by Tsukasa, et al entitled: "Alkylation of alpha, beta-unsaturated cyclic ketones. Synthesis of jasmones". In this case cis and trans jasmones are synthesized by reation of 3-methyl-2-cyclopentenone with an alkyl halide in the presence of powdered potassium hydroxide and dimethyl sulfoxide. Since the Chemical Abstract synthesis is carried out with dimethyl sulfoxide and does not involve the use of a "phase transfer agent" the reaction system of the instant invention is different in kind from the reaction system of the Chemical Abstracts paper.

THE INVENTION

The invention accordingly comprises the novel process and steps, specific embodiments of which are also described hereinafter by use of experiments and in accordance with what is now the preferred practice of the invention.

The process of our invention comprises reacting 3-methyl cyclopentenone-2 with cis-pent-2-enyl-1-halide in the presence of one or more inert solvents, aqueous alkali metal hydroxides and in the presence of one or more "phase transfer agents". The reaction is carried out in a two phase system. Thus, the invention is illustrated by the following reaction:

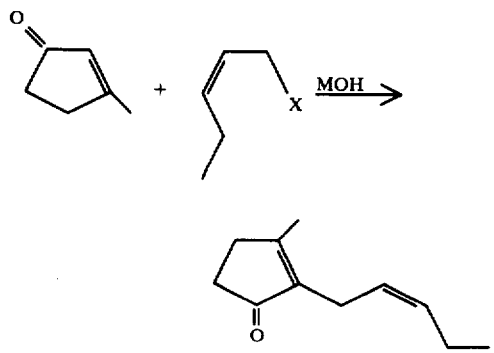

wherein X is chloro or bromo and M is alkali metal.

More specificaly, our invention provides a process for the alkenylation of 3-methyl-cyclopentenone-2 under the influence of a base comprising the step of placing the reactants for the process and the base respectively in two immiscible phases; an organic phase and either (i) an aqueous base phase or (ii) a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in out invention are as follows:

Tricapryl methyl ammonium chloride;
Cetyl trimethyl ammonium bromide; and
Benzyl trimethyl ammonium hydroxide.

In general, the "phase transfer agents" most preferred have the generic formula:

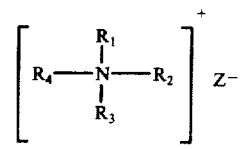

wherein at least one of $R_1$, $R_2$, $R_3$ and $R_4$ is $C_6$-$C_{14}$ aryl, $C_6$-$C_{10}$ aralkyl, $C_6$-$C_{20}$ alkyl, $C_6$-$C_{14}$ alkaryl and $C_6$-$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and $Z-$ is an anion such as chloride, bromide and hydroxide.

The process of our invention is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene.

The process of our invention is carried out at a temperature in the range of from about 10° C up to about 150° C with a temperature range of 30–120° C being preferred. The reaction time is inversely proportional to the reaction temperature, with lower reaction temperature giving rise to greater reaction times; and, accordingly, the reaction time ranges from about 30 minutes up to about 10 hours.

In the reaction of our invention the mole ratio or 3-methyl cyclopentenone-2 to cis-pent-2-enyl-1-halide is in the range of from 0.5:1.5 up to about 1.5:0.5 with a preferred ratio of 3-methyl cyclopentenone-2 to cis-pent-2-enyl-1-halide being from about 1:1 up to about 1:1.2.

The mole ratio of base to cis-pent-2enyl-1-halide in the reaction mass may be in the range of from about 0.75:1 up to about 1.5:1 with a preferred ratio of base:-cis-pent-2-enyl-1-halide being from about 1:1 up to about 1.2:1.

The quantity of "phase transfer agent" in the reaction mass based on the amount of 3-methyl cyclopentenone-2 in the reaction mass may vary from 0.5 grams per mole of 3-methyl cyclopentenone-2 up to 25 grams of "phase transfer agent" per mole of 3-methyl cyclopentenone-2 with a preferred concentration of "phase transfer agent" being in the range of from about 2.5 up to about 7.5 grams of "phase transfer agent" per mole of 3-methyl cyclopentenone-2.

The reaction of our invention is preferably carried out at atmospheric pressure since that is the most convenient condition. However, lower or higher pressures can be used without detrimentally affecting the ultimate yield of desired product.

The particular base used in the reaction is not critical, but, preferred are, sodium hydroxide and potassium hydroxide.

The following Examples I and II serve to illustrate embodiments of our invention as it is now preferred to practice it. Example III illustrates a utility of the compound produced according to the process of our invention. It will be understood that these Examples are illustrative and restricted thereto only as defined in the appended claims.

EXAMPLE I

PREPARATION OF CIS-JASMONE

Into a 250 ml reaction flask equipped with heating mantle, condenser, stirrer, thermometer and addition funnel is placed a solution of 21.3 grams of sodium hydroxide and 21.3 grams of water. Twenty grams of toluene and 1.5 grams of tricapryl methyl ammonium chloride (ALIQUAT 336®, produced by the General Mills Chemicals, Inc.) are then added to the mixture. The reaction mass is then heated to reflux (102° C) and, over a one hour period, a mixture of 35 grams of cis-pent-2-enyl-1-chloride and 24.5 grams of 3-methyl cyclopentenone-2 is added to the reaction mass while refluxing. The reaction mass is then refluxed for an additional 4 hour period, after which time it is mixed with 100 ml cold water and transferred to a separator funnel.

The organic layer is separated, washed neutral and the solvent stripped off.

The residual oil is then retained for admixture with the reaction product of Example II prior to distillation.

EXAMPLE II

PREPARATION OF CIS-JASMONE

Into a 1 liter reaction flask equipped with heating mantle, condenser, thermometer, addition funnel and stirrer is placed a solution of 106.5 grams of sodium hydroxide in 106.5 grams of water. 100 Grams of toluene and 7.5 grams of tricapryl methyl ammonium chloride are then added to the mixture. The mixture is heated to reflux and over a 1 hour period, a mixture of 122.5 grams of 3-methyl cyclopentenone-2 and 175 grams of cis pent-2-enyl-1-chloride is added to the reaction mass. The reaction mass is then refluxed for a period of two hours, after which time 250 ml water is added thereto and the resulting mixture is transferred to a separatory funnel.

The organic layer is separated, washed neutral and the solvent is stripped off.

The residual oil is then bulked with the product of Example I and the resulting product is combined with 17 grams of Primol ®, 7 grams of triethanolamine and rushed over to yield the following fractions:

| Fraction No. | Vapor Temperature (° C) | Liquid Temperature (° C) | Vacuum mm | Weight (g) |
|---|---|---|---|---|
| 1 | 43-120 | 91-159 | 2.6 | 27.3 |
| 2 | 125 | 162 | 2.6 | 19.0 |
| 3 | 167 | 185 | 2.6 | 18.3 |
| 4 | 184 | 201 | 2.5 | 19.4 |
| 5 | 203 | 217 | 2.5 | 16.4 |

-continued

| Fraction No. | Vapor Temperature (° C) | Liquid Temperature (° C) | Vacuum mm | Weight (g) |
|---|---|---|---|---|
| 6 | 220 | 240 | 2.5 | 26.9 |

Fractions 1, 2 and 3 of the rushed over material, are then bulked and the bulked material is combined with 2 grams of Primol ® and Ionox ®. The resulting material is then fractionally distilled on a 12 plate Vigreaux column yielding the following fractions:

| Fraction No. | Vapor Temperature (° C) | Liquid Temperature (° C) | Vacuum mm | Weight (g) |
|---|---|---|---|---|
| 1 | 53 | 107 | 3.5 | 4.8 |
| 2 | 36 | 100 | 1.0 | 4.5 |
| 3 | 72 | 120 | 0.8 | 3.1 |
| 4 | 80 | 121 | 0.8 | 4.0 |
| 5 | 80 | 123 | 1.0 | 4.9 |
| 6 | 78 | 122 | 1.2 | 4.2 |
| 7 | 79 | 128 | 1.2 | 3.8 |
| 8 | 79 | 137 | 1.2 | 4.6 |
| 9 | 79 | 144 | 1.2 | 3.9 |
| 10 | 87 | 151 | 1.2 | 2.3 |
| 11 | 97 | 159 | 1.2 | 4.1 |
| 12 | 98 | 174 | 1.2 | 3.8 |
| 13 | 112 | 182 | 1.2 | 2.4 |
| 14 | 120 | 204 | 1.2 | 1.9 |
| 15 | 125 | 250 | 1.2 | 2.6 |

Fractions 6-9 are bulked, analyzed and evaluated. NMR, IR and Mass Spectral analyses yield the result that the product is 94% cis-jasmone having the structure.

Figure 2:
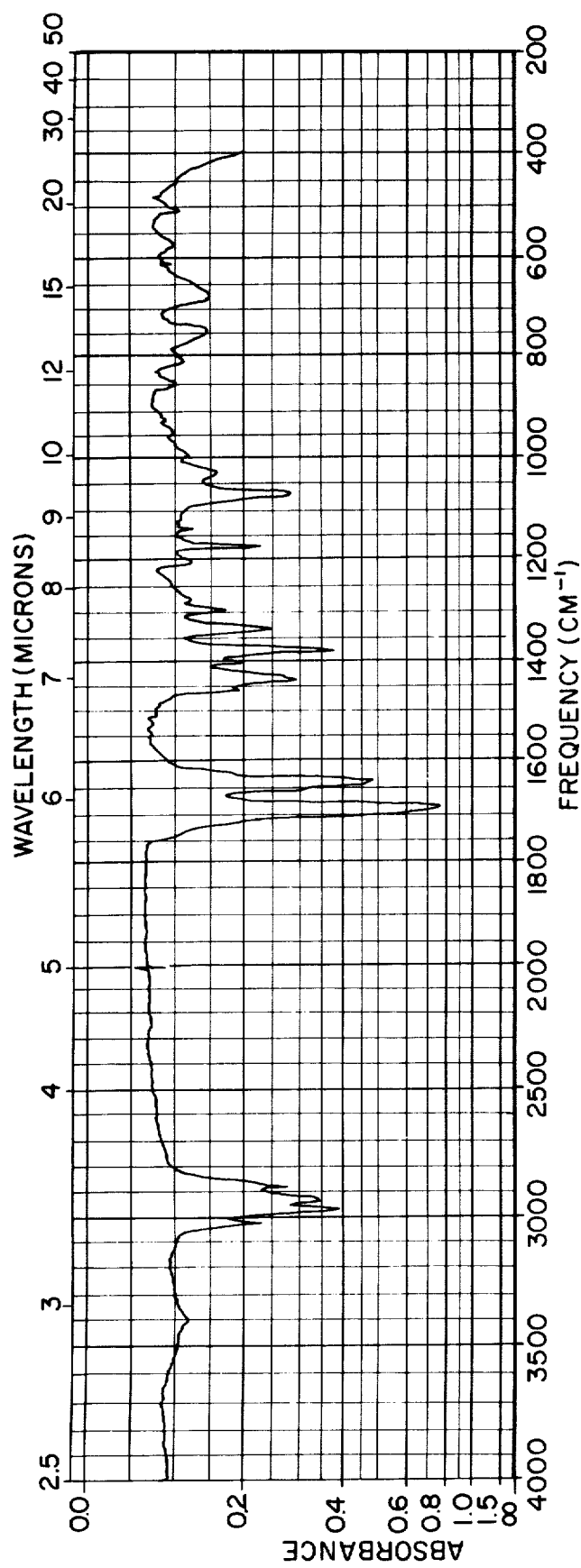

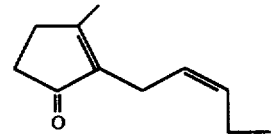

and the remainder, trans jasmone. The NMR spectrum is set forth in FIG. 1. The IR spectrum is set forth in FIG. 2.

EXAMPLE III

JASMINE PERFUME

The following mixture is prepared:

| Ingredient | Parts by Weight |
|---|---|
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmin Lactone | 20 |
| Dihydromethyl Jasmonate | 10 |
| Linalool | 150 |
| Benzyl Acetate | 400 |
| Abietyl Alcohol | 150 |
| Cis Jasmone (Produced according to Example II; bulked fractions 6-9) | 50 |

The cis-jasmone, produced according to Example II, imparts to this jasmine formulation the green, sweet, celery-like note so important to the jasmine perfume formulation.

What is claimed is:

1. A process for producing cis-jasmone having the structure:

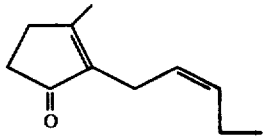

comprising the step of intimately admixing 3-methyl cyclopentenone-2 having the structure:

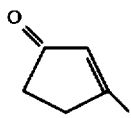

with a cis pentenyl halide having the structure:

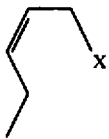

in the presence of a base and a "phase transfer agent" having the generic formula:

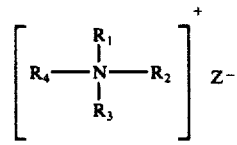

wherein at least one of $R_1$, $R_2$, $R_3$ and $R_4$ is $C_6$-$C_{14}$ aryl, $C_6$-$C_{10}$ aralkyl, $C_6$-$C_{20}$ alkyl, $C_6$-$C_{14}$ aralkyl and $C_6$-$C_{20}$ alkenyl and the other of $R_2$, $R_3$ and $R_4$ is $C_1$-$C_8$ alkyl, and Z⁻ is an anion selected from the group consisting of halogen anion and hydroxyl anion and wherein X is chloro or bromo, said reaction being carried out in a two liquid phase system; the reaction temperature being in the range of from 30° C up to 120° C; the mole ratio of 3-methyl cyclopentenone-2:cis-pent-2-enyl halide being in the range of from 0.5:1.5 up to about 1.5:0.5; the concentration of "phase transfer agent" in the reaction mass based on the amount of 3-methyl cyclopentenone-2 being in the range of from 0.5 grams of phase transfer agent per mole of 3-methyl cyclopentenone-2 up to 25 grams of phase transfer agent per mole of 3-methyl cyclopentenone-2; the reaction being carried out in a solvent inert to the reaction system, selected from the group consisting of toluene, benzene, o-xylene, m-xylene, p-xylene, ethyl benzene, n-hexane and cyclohexane; and then fractionally distilling the resulting product whereby a residue and a distillate are formed; and recovering said cis-jasmone from said distillate.

2. The process of claim 1, wherein the base is an alkali metal hydroxide.

3. The process of claim 2, wherein the mole ratio of base:cis-pent-2-enyl-1-halide is in the range of from 0.75:1 up to about 1.5:1.

4. The process of claim 1, wherein the cis-pent-2-enyl-1-halide is cis-pent-2-enyl-1-chloride.

* * * * *